(12) United States Patent
Kuwayama et al.

(10) Patent No.: US 7,316,896 B2
(45) Date of Patent: Jan. 8, 2008

(54) EGG FREEZING AND STORING TOOL AND METHOD

(75) Inventors: Masashige Kuwayama, Tokyo (JP); Futoshi Inoue, Fujinomiya (JP)

(73) Assignee: Kabushiki Kaisha Kitazato Supply, Fujinomiya-Shi, Shizuoka (JP)

( * ) Notice: Subject to any disclaimer, the term of this patent is extended or adjusted under 35 U.S.C. 154(b) by 684 days.

(21) Appl. No.: 10/824,605

(22) Filed: Apr. 15, 2004

(65) Prior Publication Data

US 2004/0259072 A1 Dec. 23, 2004

(30) Foreign Application Priority Data

Apr. 15, 2003 (JP) .............................. 2003-110496
Sep. 30, 2003 (JP) .............................. 2003-340496

(51) Int. Cl.
*A01N 1/00* (2006.01)
*A01N 1/02* (2006.01)
*C12N 5/00* (2006.01)
*C12N 5/06* (2006.01)
*C12N 5/08* (2006.01)
*C12N 1/04* (2006.01)
*A61D 19/00* (2006.01)
*C12M 1/00* (2006.01)
*C12M 3/00* (2006.01)
*F25B 21/02* (2006.01)
*B01L 3/00* (2006.01)
*B01L 3/02* (2006.01)

(52) U.S. Cl. .................... 435/1.3; 435/307.1; 435/325; 435/366; 435/260; 435/374; 422/102; 422/100

(58) Field of Classification Search ............ 435/307.1, 435/1.3, 325, 366, 260, 374; 800/24; 422/102, 422/100

See application file for complete search history.

(56) References Cited

U.S. PATENT DOCUMENTS 4,799,358 A 1/1989 Knopf et al.

(Continued)

FOREIGN PATENT DOCUMENTS

EP 1121015 6/2004

(Continued)

OTHER PUBLICATIONS

Vajta G., Holm P., Kuwayama M., Booth P.J., Jacobsen H., Greve T., and Callesen H. Open Pulled Straw (OPS): A new way to reduce cryoinnjuries of bovine ova and embryos. 1998. Molecular Reproduction and Development 51:53-58.*

(Continued)

*Primary Examiner*—Melvin Mayes
*Assistant Examiner*—Simon Vainberg
(74) *Attorney, Agent, or Firm*—Buchanan Ingersoll & Rooney PC

(57) ABSTRACT

An egg freezing and storing instrument has an egg freezing and storing tube made of a liquid nitrogen-resistant material; and a metal cylindrical protection member for protecting the tube. The tube has a body part; and an egg-storing small-diameter part having an inner diameter of 0.1 mm to 0.5 mm. The tube can be heat-sealed at a front side of the small-diameter part and at a rear side of the body part. The cylindrical protection member has a tubular part for accommodating a front side of the small-diameter part of the tube; and a semi-tubular part for accommodating a portion of the small-diameter part not accommodated in the tubular part and a front portion of the body part.

9 Claims, 15 Drawing Sheets

U.S. PATENT DOCUMENTS

| | | | | |
|---|---|---|---|---|
| 5,127,693 | A * | 7/1992 | Pruit | 294/15 |
| 5,217,693 | A * | 6/1993 | Anderson et al. | 422/100 |
| 5,283,170 | A * | 2/1994 | Cassou et al. | 435/1.3 |
| 5,545,562 | A * | 8/1996 | Cassou et al. | 435/307.1 |
| 6,503,698 | B1 * | 1/2003 | Dobrinsky et al. | 435/1.3 |
| 6,590,139 | B1 * | 7/2003 | Lee et al. | 800/24 |
| 2003/0236517 | A1 * | 12/2003 | Appling | 606/7 |

FOREIGN PATENT DOCUMENTS

| | | | |
|---|---|---|---|
| FR | WO-83/02386 | * | 7/1983 |
| JP | 2000-189155 | | 7/2000 |
| JP | 2001-252293 | | 9/2001 |
| JP | 2002-315573 | | 10/2002 |
| WO | WO 00/21365 | | 4/2000 |
| WO | WO02/085110 | | 10/2002 |

OTHER PUBLICATIONS

Kuleshova L.L., Shaw J.M. A strategy for rapid cooling of mouse embryos within a double straw to eliminate the risk of contamination during storage in liquid nitrogen. 2000. Human Reproduction. 15 (12): 2604-2609.*

Vanderzwalmen P., Bertin G., Debauche Ch., Standaert V., Bollen N., Roosendaal E., Vandervorst M., Schoysman R., and Zech N. 2003. Vitrification of human blastocysts with the Hemi-Straw carrier: application of assisted hatching after thawing. Human Reproduction. 18(7):1504-1511.*

Liebermann J and Tucker M.J. Effect of carrier system on the yield of human oocytes and embryos as assessed by survival and developmental potential after vitrification. 2002. Reproduction.124: 1-7.*

Liebermann J. Recent developments in humane oocyte, embryo and blastocyst vitrification: where are we now? 2003 Reproductive BioMedicine Online. 7(6):623-633.*

Letur-Konirsh H., Collin G., Sifer C., Devaux A., Kutten F., Madelenar P., Brun-Vezinet F., Feldmann G., and Benifla J-L. Safety of cryopreservation straws for human gametes or embryos: a study with human immunodeficiency virus-1 under cryopreservation conditions. 2003. Human Reproduction. 18(1):140-144.*

* cited by examiner

F I G. 8
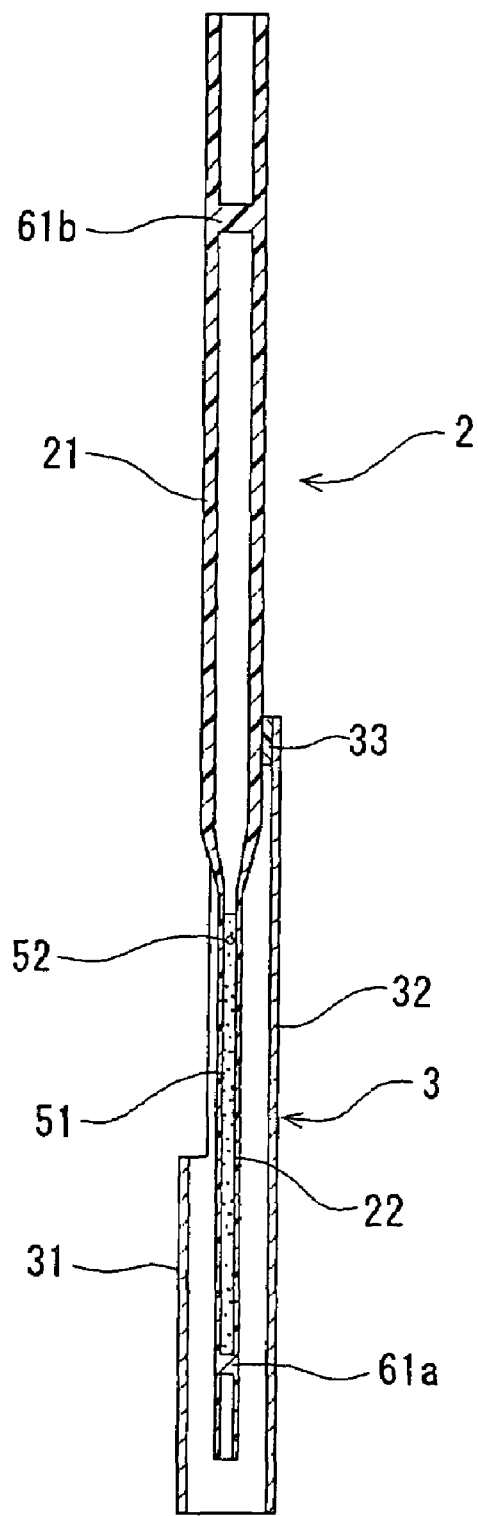

EGG FREEZING AND STORING TOOL AND METHOD

BACKGROUND OF THE INVENTION

1. Field of the Invention

The present invention relates to an egg freezing and storing instrument used to freeze and store eggs such as ova and mammalian embryos and a method to be carried out in using the egg freezing and storing instrument.

2. Description of the Related Art

Freezing and storing the mammalian embryo enables conservation of hereditary resources of specific systems and kinds, is effective for maintaining animals standing on the brink of ruin, and is useful for coping with sterility.

As disclosed in Japanese Patent Application Laid-Open No. 2000-189155 (patent document 1), there is proposed a method for freezing and storing mammalian embryos. In this method, mammalian embryos or ova are bonded to the inner surface of the freezing and storing container such as the sterilized frozen straw, frozen vial or frozen tube by using a vitrified liquid in an amount minimum and enough to enclose the mammalian embryos or the ova therewith. The freezing and storing container is sealed and rapidly cooled by bringing the freezing and storing container into contact with liquid nitrogen. In the thawing method of this proposal, the freezing and storing container stored in the above method is taken out of the liquid nitrogen and one end thereof is opened. A diluted liquid of 33 to 39° C. is injected directly into the container to thaw the mammalian embryos or the ova and dilute the vitrified liquid. This method eliminates a possibility that the mammalian embryos or the ova are infected with a disease through viruses or bacteria and is capable of storing them at a high survival rate and thawing them and diluting the vitrified liquid.

The present applicant proposed the egg freezing and storing instrument, as disclosed in Japanese Patent Application Laid-Open No. 2002-315573 (patent document 2). The egg freezing and storing instrument includes the body part made of a cold-proof material; the strip, made of a material flexible, transparent, and resistant to liquid nitrogen, mounted at one end of the body part to hold eggs attached thereto; and the cylindrical member which is made of a cold-proof material and whose one end is sealed. The cylindrical member allows the egg-holding strip to be endosably mounted on the body part.

As disclosed in Japanese Patent Application Laid-Open No. 2001-252293 (patent document 3), there is proposed a tool for vitrifying eggs or embryos. The vitrifying tool has the cylindrical super-fine tubular part; and the connection part, continuous with the super-fine tubular part, to be mounted on the sucking and discharging tool. The minimum distance between the opposed two points on the inner surface, of the super-fine tubular part, vertical to the longitudinal direction thereof is shorter than the double of the minimum outer diameter of one ovum or one embryo and longer than the maximum diameter thereof. Therefore two or more ova or embryos are incapable of being present side by side on the inner surface of the super-fine tubular part vertical to the longitudinal direction thereof.

The method of the patent document 1 is effective for storing embryos or ova, but there is a demand for development of a freezing and storing instrument that can be operated easily.

The egg freezing and storing instrument of the patent document 2 has an advantage of collecting eggs very easily, but causes the eggs to contact the liquid nitrogen directly. Thus the egg freezing and storing instrument has a problem that the eggs are adversely affected by the liquid nitrogen.

The vitrifying tool of the patent document 3 has the effect that ova or embryos can be cooled rapidly because the ova or the embryos are collected and cooled inside the super-fine tubular part. However, there is a possibility that bacteria enter the vitrifying tool when a pipette which has collected the ova or the embryos from the vitrifying tool is separated therefrom. The vitrifying tool has another problem that the super-fine tubular part may be damaged in immersing the vitrifying tool in the liquid nitrogen. Another problem of the vitrifying tool is that it is necessary to perform a difficult work because the super-fine tubular part is required to be inserted into a storing outer cylinder in the presence of the liquid nitrogen.

Therefore it is an object of the present invention to provide an egg freezing and storing instrument and method capable of preventing permeation of bacteria into a tube of the tool, while an operation of freezing (vitrifying) and storing an egg in a liquid nitrogen tank is being performed; cooling the egg rapidly without bringing the egg into direct contact with liquid nitrogen, and keeping the egg in a stable state in the liquid nitrogen tank.

SUMMARY OF THE INVENTION

To overcome the above-described problems, there is provided an egg freezing and storing instrument including an egg freezing and storing tube which is made of a liquid nitrogen-resistant material and can be heat-sealed; and a metal cylindrical protection member for protecting the egg freezing and storing tube. The egg freezing and storing tube includes a body part; an egg-storing small-diameter part having a smaller outer diameter than the body part and having an inner diameter of 0.1 mm to 0.5 mm; a front-side heat-sealable portion at which the small-diameter part can be heat-sealed at a front side of the small-diameter part after an egg is collected in the egg-storing small-diameter part thereof; and a rear-side heat-sealable portion at which the body part can be heat-sealed at a rear side thereof, after the egg is collected in the egg-storing small-diameter part. The cylindrical protection member has a tubular part for accommodating the front side of the small-diameter part of the egg freezing and storing tube; and a semi-tubular part for accommodating a portion of the small-diameter part of the egg freezing and storing tube not accommodated in the tubular part and a front portion of the body part.

To overcome the above-described problems, there is provided an egg freezing and storing instrument including an egg freezing and storing tube which is made of a liquid nitrogen-resistant material and can be heat-sealed; and a metal cylindrical protection member mounted on the egg freezing and storing tube, for protecting the egg freezing and storing tube. The egg freezing and storing tube includes a body part; an egg-storing small-diameter part having a smaller outer diameter than the body part; a front-side heat-sealable portion at which the small-diameter part can be heat-sealed at a front side of the small-diameter part after an egg is collected in the egg-storing small-diameter part; and a rear-side heat-sealable portion at which the body part can be heat-sealed at a rear side thereof after the egg is collected in the egg-storing small-diameter part. The cylindrical protection member has a tubular part for accommodating the front side of the small-diameter part of the egg freezing and storing tube; a semi-tubular part, disposed at a rear end of the tubular part, for accommodating a portion of the small-diameter part of the egg freezing and storing tube not accommodated in the tubular part and a front portion of the body part; and a holding part, disposed at a rear end of the semi-tubular part, for holding the body part of the egg freezing and storing tube. The cylindrical protection member is slidable to a rear side of the egg freezing and storing tube to allow the small-diameter part to be exposed to the outside from a front end of the cylindrical protection member. The egg freezing and storing tube has a slip-off prevention part, for preventing the cylindrical protection member from slipping off from the front side of the egg freezing and storing tube, formed on the body part thereof or in the vicinity of a boundary between the body part thereof and the small-diameter part thereof.

BRIEF DESCRIPTION OF THE DRAWINGS

FIG. 8 is an explanatory view for explaining an operation of the egg freezing and storing instrument of the present invention.

DETAILED DESCRIPTION OF THE PREFERRED EMBODIMENTS

The embodiments of the egg freezing and storing instrument of the present invention will be described below with reference to drawings.

Figure 1:
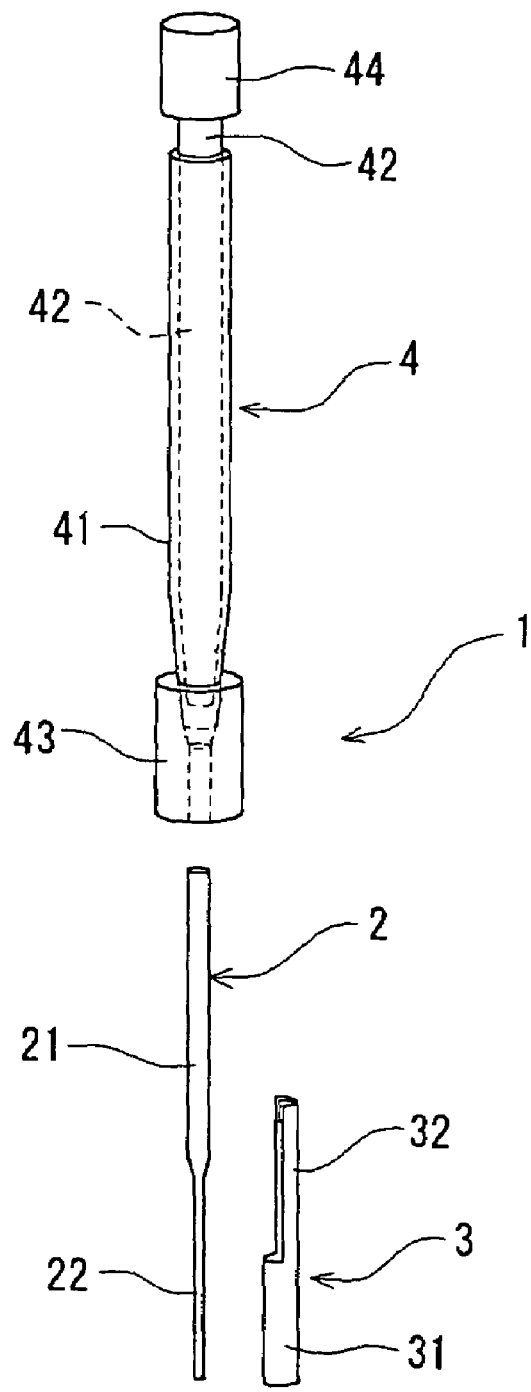
FIG. 1 is a perspective view showing an embodiment of an egg freezing and storing instrument of the present invention.
Figure 2:
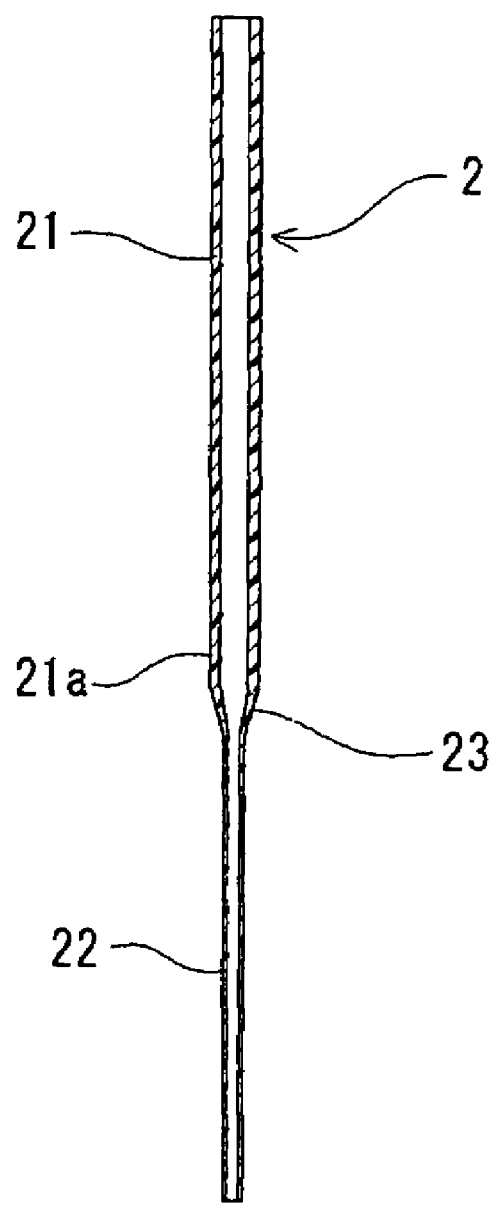
FIG. 2 is an enlarged side view showing an egg freezing and storing tube for use in the egg freezing and storing instrument shown in FIG. 1.

FIG. 1 is a perspective view showing an embodiment of an egg freezing and storing instrument of the present invention. FIG. 2 is an enlarged side view showing an egg freezing and storing tube for use in the egg freezing and storing instrument shown in FIG. 1.

An egg freezing and storing instrument 1 of the present invention has an egg freezing and storing tube 2 which is made of a liquid nitrogen-resistant material and can be heat-sealed; and a metal cylindrical protection member 3, made of the liquid nitrogen-resistant material, for protecting the egg freezing and storing tube 2. The egg freezing and storing tube 2 has a body part 21 and an egg-storing small-diameter part 22 having a smaller outer diameter than the body part 21 and having an inner diameter of 0.1 mm to 0.5 mm. The egg freezing and storing tube 2 has a front-side heat-sealable portion at which the small-diameter part 22 can be heat-sealed at a front side of the small-diameter part 22; and a rear-side heat-sealable portion at which the body part 21 can be heat-sealed at a rear side thereof, after an egg is collected in the egg-storing small-diameter part 22. The cylindrical protection member 3 has a tubular part 31 for accommodating the front side of the small-diameter part 22 of the egg freezing and storing tube 2; and a semi-tubular part 32 for accommodating a portion of the small-diameter part 22 of the egg freezing and storing tube 2 not accommodated in the tubular part 31 and a front portion 21a of the body part 21.

It is preferable that the egg freezing and storing instrument 1 has an egg-collecting sucking tool 4 having a front portion to which a rear end of the body part 21 of the egg freezing and storing tube 2 can be connected.

The egg freezing and storing instrument 1 of this embodiment has the egg freezing and storing tube 2, the cylindrical protection member 3, and the egg-collecting sucking tool 4.

As shown in FIGS. 1 and 2, the egg freezing and storing tube 2 has the body part 21, the egg-storing small-diameter part 22 having a smaller diameter than the body part 21, and a tapered part 23 interposed between the body part 21 and the egg-storing small-diameter part 22.

The full length of the egg freezing and storing tube 2 is set to favorably 50 to 100 mm, more favorably 60 to 90 mm, and most favorably 70 to 80 mm. The length of the body part 21 is set to favorably 20 to 70 mm and more favorably 30 to 60 mm. The inner diameter of the body part 21 is set to favorably 1.0 to 3.0 mm and more favorably 1.5 to 2.5 mm. The thickness of the body part 21 is set to favorably 50 to 400 µm and more favorably 100 to 300 µm. The length of the small-diameter part 22 is set to favorably 20 to 50 mm and more favorably 30 to 40 mm.

The inner diameter of the small-diameter part 22 is set to 0.1 to 0.5 mm and favorably 0.1 to 0.3 mm. The thickness of the small-diameter part 22 is set to favorably 10 to 300 µm and more favorably 25 to 200 µm. It is favorable that the thickness of the small-diameter part 22 is set smaller than that of the body part 21. A outer diameter and thickness transition region is formed in the tapered part 23. More specifically, in the tapered part 23, the outer diameter, inner diameter, and thickness of the tube 2 become smaller toward the small-diameter part 22. The tapered part 23 is formed to prevent the tube 2 from kinking at the boundary between the body part and the small-diameter part.

The body part 21 has substantially the same outer diameter over the full length thereof. The egg-storing small-diameter part 22 has also the substantially same outer diameter over the full length thereof. Each of the body part and the egg-storing small-diameter part may be gently tapered off to the front end thereof.

The tube 2 is made of the liquid nitrogen-resistant material and can be heat-sealed. The following thermoplastic resins are used as the material for the tube 2: polyester (for example, polyethylene terephthalate, polybutylene terephthalate); polyolefin (for example, polyethylene, ultra-high-molecular-weight polyethylene, polypropylene, ethylene-propylene copolymer, ethylene-vinyl acetate copolymer), styrene resin (for example, polystyrene, methacrylate-styrene copolymer, methacrylate-butylene-styrene copolymer); and polyamide (for example, nylon 6, nylon 66).

The tube 2 may consist of a plurality of layers. A highly heat-sealable resin is preferable for an inner layer of the tube 2. For example, a low-molecular-weight polyethylene is preferable. Unstretched low-molecular-weight polyethylene is particularly preferable. The inner layer may be formed only at the heat-sealable portion (front-side and rear-side heat-sealable portions). As the material for the outer layer of the tube 2, it is possible to use the above-described thermoplastic resins; and hardly heat-sealable resins such as fluorocarbon and polyimide. As the fluorocarbon resin, it is possible to use polytetrafluoroethylene, ethylene-tetrafluoroethylene copolymer, tetrafluoroethylene-hexafluoropropylene copolymer, and chlorotrifluoroethylene. Aromatic polyimide is preferable as the polyimide. The material for the outer layer of the tube 2 may be mono-axially or biaxially stretched.

The egg freezing and storing tube 2 has the front-side heat-sealable portion at which the small-diameter part 22 can be heat-sealed at the front side thereof and the rear-side heat-sealable portion at which the body part 21 can be heat-sealed at the rear side thereof, after an egg is collected in the egg-storing small-diameter part 22 thereof. In this embodiment, the tube 2 can be heat-sealed at every portion thereof. However, the heat-sealable portion is not limited to this construction. For example, as the heat-sealable portion (easy-to-seal portion), a thin portion which is to be heat-sealed may be formed at the front side of the small-diameter part 22 and at the rear side of the body part 21. As another example of the heat-sealable portion, an inner layer made of a heat-sealable material may be formed at the front side of the small-diameter part 22 and at the rear side of the body part 21.

Figure 5:
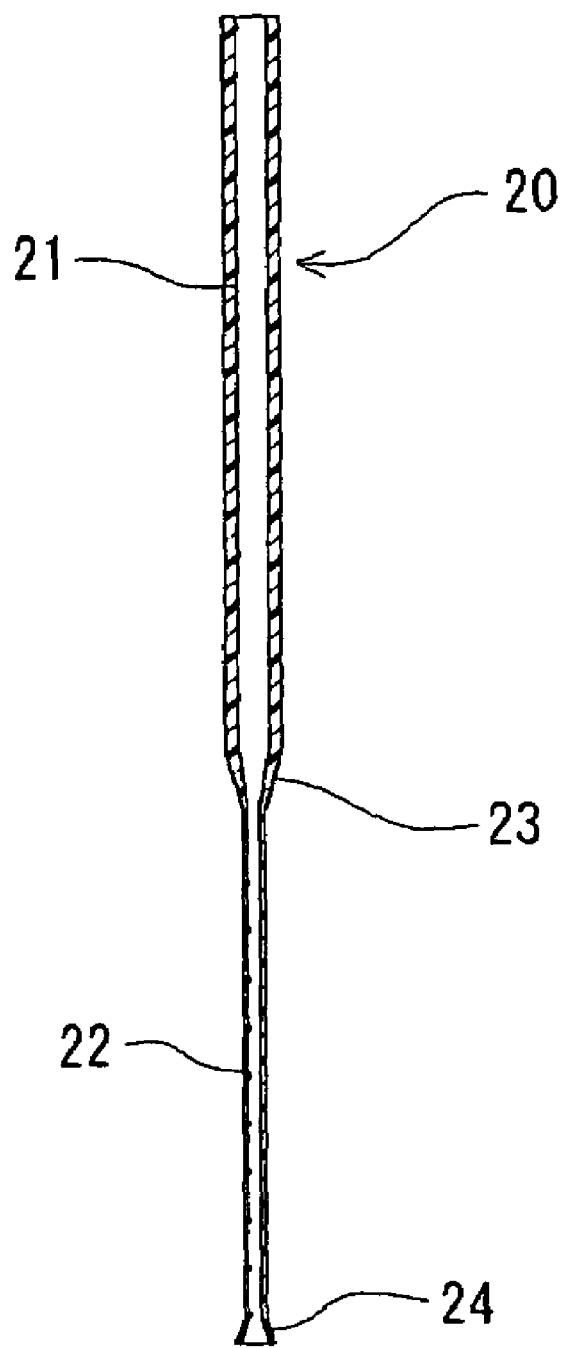
FIG. 5 is an enlarged side view showing another example of an egg freezing and storing tube for use in the egg freezing and storing instrument of the present invention.

As shown in FIG. 5, an egg freezing and storing tube 20 may have a diameter-widened part 24 at the front end thereof. It is preferable that the diameter of the diameter-widened part 24 becomes gradually larger toward the front end thereof. It is preferable that the length of the diameter-widened part 24 is 0.5 to 3 mm. The maximum inner diameter of the diameter-widened part 24 is set to favorably 1.5 to 10 times as large as the inner diameter of the egg-storing small-diameter part 22 and more favorably twice to seven times as large as the inner diameter of the egg-storing small-diameter part 22. The formation of the diameter-widened part 24 facilitate an egg collection work, reduces the opportunity in which the front end surface of the tube 20 contacts the egg when the egg is collected, and reduces the opportunity in which the front end surface of the tube 20 is damaged.

The metal cylindrical protection member 3 has the tubular part 31 disposed at the front side thereof and the semi-tubular part 32 disposed at the rear side thereof. The tubular part 31 accommodates the front side of the small-diameter part 22 of the egg freezing and storing tube 2. The semi-tubular part 32 accommodates the portion of the small-diameter part 22 not accommodated in the tubular part 31 and the front portion 21a of the body part 21. The semi-tubular part 32 may be so formed as to accommodate almost all of the body part 21.

The cylindrical protection member 3 protects the tube 2 which has collected the egg, together with a vitrified fluid without inhibiting cooling of the egg. Therefore when the cylindrical protection member 3 is mounted on the tube 2, the collected egg-disposed range of small-diameter part 22 between the central position thereof and the rear end thereof is located within the length of the semi-tubular part 32. That is, the cylindrical protection member 3 is mounted on the tube 2 in such a way that the small-diameter part 22 accommodating the collected egg is exposed to the outside and easily capable of contacting liquid nitrogen. The cylindrical protection member 3 is mounted on the tube 2 with the front end of the tube 2 unprojecting from the front end of the tubular part 31. Thus when the tube 2 on which the protection member 3 has been mounted is introduced into a liquid nitrogen-filled container from the small-diameter part 22, the front end of the small-diameter part 22 of the tube 2 does not contact the bottom surface of the liquid nitrogen-filled container. Therefore it is possible to prevent the tube 2 from kinking at the small-diameter part 22 or the tapered part 23 and thus prevent the tube 2 from being damaged.

The full length of the protection member 3 is set to favorably 30 to 70 mm, more favorably 40 to 60 mm, and most favorably 45 to 55 mm. The length of the tubular part 31 is set to favorably 10 to 40 mm, more favorably 10 to 30 mm, and most favorably 15 to 25 mm. The inner diameter of the tubular part 31 is set to favorably 2.0 to 4.0 mm and more favorably 2.5 to 3.5 mm. It is favorable that the tubular part 31 is circular, as shown in the drawings. But the tubular part 31 may be elliptically cylindrical or polygonally cylindrical. The thickness of the tubular part 31 is set to favorably 0.3 to 1.0 mm.

The length of the semi-tubular part 32 is set to favorably 10 to 40 mm and more favorably 25 to 35 mm. It is favorable that the length of the inner circumference of the semi-tubular part 32 is ⅓ to ⅔ as small as that of the length of the inner circumference of the tubular part 31. It is favorable that the body part 21 of the tube 2 can be accommodated in the semi-tubular part 32 from the side face of the semi-tubular part 32. That is, the tube 2 can be mounted on the protection member 3 not from the opening disposed at the rear end of the semi-tubular part 32 but from the axially long opening formed at the side face thereof. It is preferable that the semi-tubular part 32 is semicylindrical, as shown in the drawings. But the semi-tubular part 32 may be semi-elliptically tubular or semi-polygonally tubular.

The cylindrical protection member 3 is made of metal. As metal, it is possible to use stainless steel, aluminum, an aluminum alloy, titanium, and a titanium alloy. In addition, high specific-gravity resin can be used. As the high specific-gravity resin, a mixture of a resinous material and metal powder applied thereto can be used. Because the metal protection member 3 has a high thermal conductivity, it is capable of rapidly cooling the egg freezing and storing tube accommodated therein and rapidly heating the egg freezing and storing tube when the egg is thawed. When the metal protection member 3 is supplied to the liquid nitrogen tank, it does not float therein. Thus the metal protection member 3 can be stored on the bottom of the tank reliably.

Figure 3:
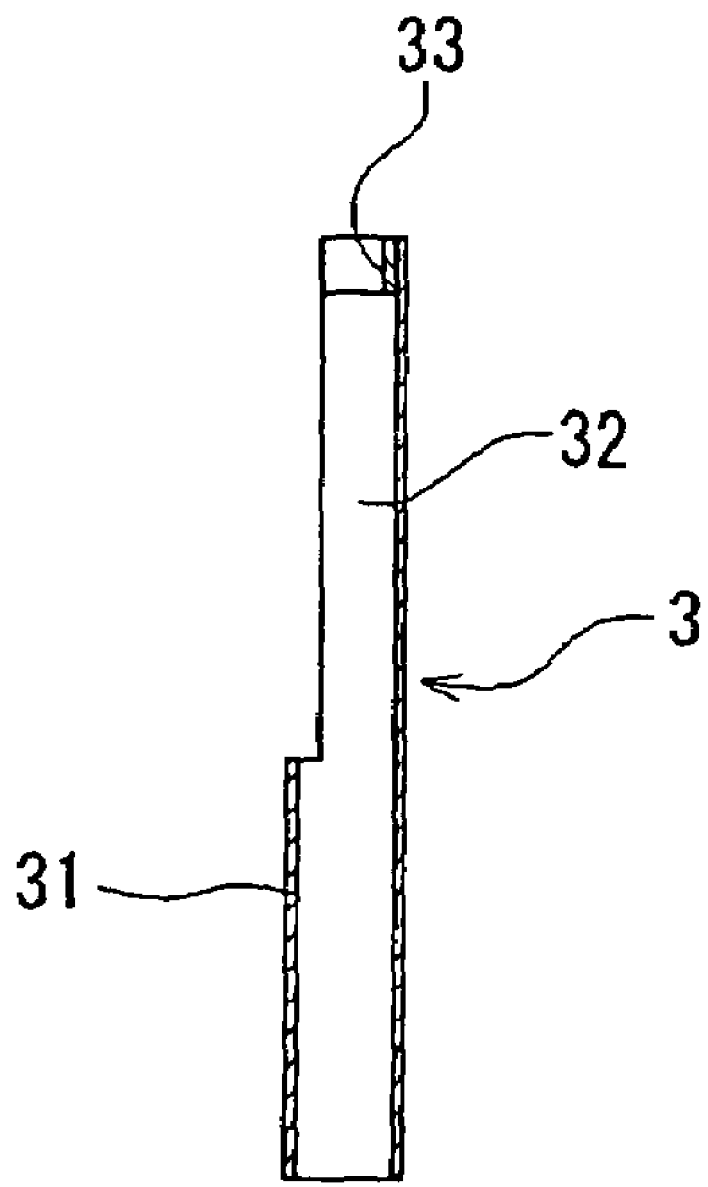
FIG. 3 is an enlarged side view showing a protection member for the egg freezing and storing tube for use in the egg freezing and storing instrument shown in FIG. 1.
Figure 4:
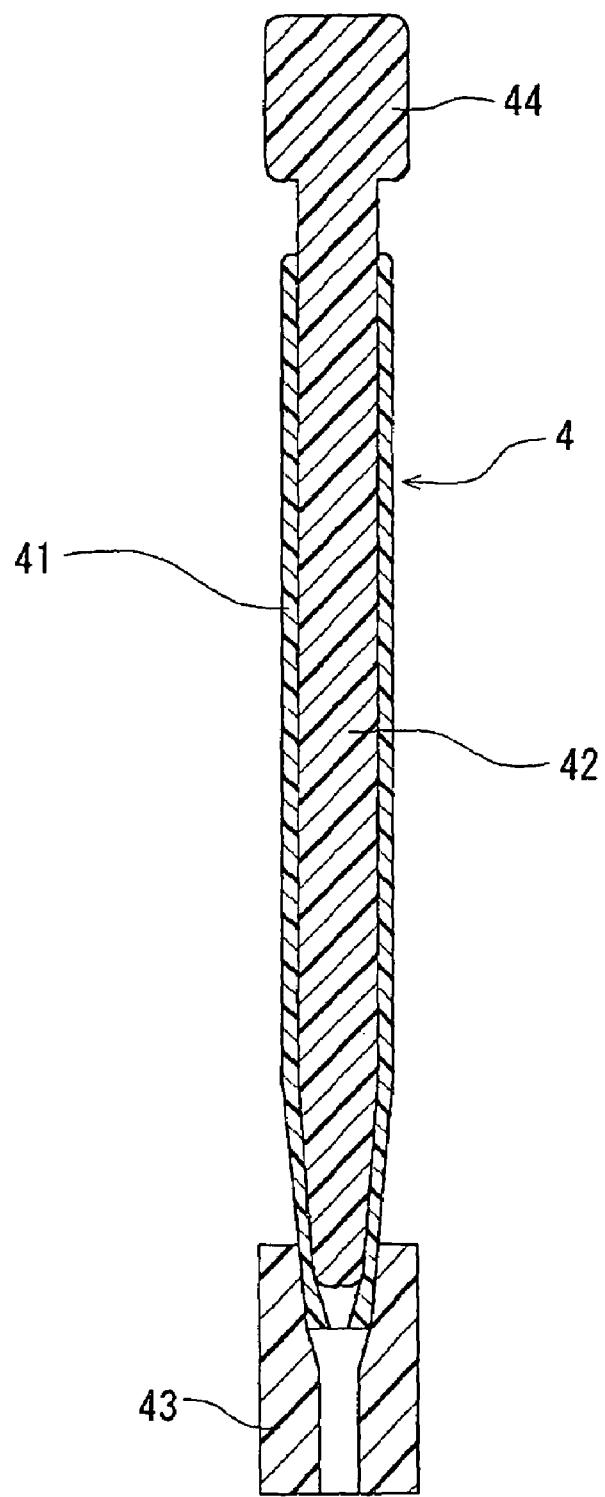
FIG. 4 is an enlarged sectional view showing a sucking tool for the egg freezing and storing tube for use in the egg freezing and storing instrument shown in FIG. 1.

It is preferable that the semi-tubular part 32 of the cylindrical protection member 3 has a holding part 33 for holding the body part 21 of the egg freezing and storing tube 2. As shown in FIG. 3, the protection member 3 of this embodiment has the holding part 33 disposed at the rear end of the semi-tubular part 32. The holding part 33 is made of an elastic material and semi-cylindrical. The holding part 33 holds the tube 2 with the holding part 33 in dose contact with the outer surface of the body part 21 of the tube 2. The holding part 33 serves as a means for preventing the movement of the protection member 3 mounted on the tube 2.

As the material for the holding part 33, it is possible to use rubber such as silicone rubber, latex rubber; and elastomers such as polyolefin elastomer, polyurethane or polyurethane elastomer, polyamide elastomer, and styrene elastomer (for example, SEBS).

The egg freezing and storing instrument 1 of this embodiment has the egg-collecting sucking tool 4 having a connection part 43 to which the rear end of the body part 21 of the egg freezing and storing tube 2 can be connected.

The egg-collecting sucking tool 4 has an outer tube 41, a plunger 42 which slides inside the outer tube 41 liquid-tightly, and the connection part 43 disposed at the front end of the outer tube 41. In this embodiment, the connection part 43 of the egg-collecting sucking tool 4 is composed of an elastic tube. The front end of the egg-collecting sucking tool 4 can be liquid-tightly connected to the rear end of the body part 21 of the egg freezing and storing tube 2. The front end of the outer tube 41 is liquid-tightly installed on the rear side of the connection part 43. The plunger 42 has an operation portion 44 formed at its rear end thereof. The egg-collecting sucking tool 4 having any constructions can be used, provided that the egg-collecting sucking tool 4 can be liquid-tightly connected to the rear end of the body part 21 of the egg freezing and storing tube 2 and can suck the egg, together with the vitrified fluid thereto.

The method of the present invention for freezing and storing an egg will be described below. The method for freezing and storing an egg is carried out in using the above-described egg freezing and storing instrument 1.

The method of the present invention for freezing and storing an egg will be described below is carried out by using the above-described egg freezing and storing instrument.

The freezing and storing method includes the steps of preparing an egg whose intracellular fluid has been replaced with an equilibrium fluid and whose extracellular fluid has been replaced with a vitrified fluid; collecting the egg into the small-diameter part 22 of the egg freezing and storing tube 2, together with the vitrified fluid; heat-sealing one side of the egg freezing and storing tube 2 at a front portion of the small-diameter part 22 and heat-sealing the other side of the egg freezing and storing tube 2 at a portion of the body part 21; mounting the metal protection member 3 on the heat-sealed egg freezing and storing tube 2; and supplying the egg freezing and storing tube 2 on which the protection member 3 has been mounted into the liquid nitrogen tank.

It is preferable that the egg freezing and storing instrument to be used in carrying out the storing method has the egg-collecting sucking tool 4 having the connection part to which the rear end of the body part 21 of the egg freezing and storing tube 2 can be connected.

The method for freezing and storing the egg to be carried out by using the egg freezing and storing instrument includes the steps of preparing an egg whose intracellular fluid has been replaced with an equilibrium fluid and whose extracellular fluid has been replaced with a vitrified fluid; preparing a unit including the egg freezing and storing tube 2 and the sucking tool 4 mounted on the body part 21 of the egg freezing and storing tube 2; collecting the egg into the small-diameter part 22 of the egg freezing and storing tube 2, together with the vitrified fluid by operating the sucking tool 4; heat-sealing one side of the egg freezing and storing tube 2 at a front portion of the small-diameter part 22 and heat-sealing the other side of the egg freezing and storing tube 2 at a portion of the body part 21 with the sucking tool 4 mounted on the egg freezing and storing tube 2; removing the sucking tool 4 from the egg freezing and storing tube 2; mounting the metal protection member 3 on the heat-sealed egg freezing and storing tube 2; and supplying the egg freezing and storing tube 2 on which the protection member 3 has been mounted into the liquid nitrogen tank.

The step of sealing the egg freezing and storing tube is performed with the sucking tool mounted on the egg freezing and storing tube. Thus it is possible to prevent bacteria from penetrating into the tube in which the egg has been collected.

The method of freezing and storing an egg will be described below by exemplifying the case in which an ovum is frozen to store them.

Initially the ovum is collected at the tip of a pipette. Thereafter a work of replacing the intracellular fluid of the ovum with the equilibrium fluid is performed. Then a work of replacing the extracellular fluid with the vitrified fluid is performed.

Figure 6:
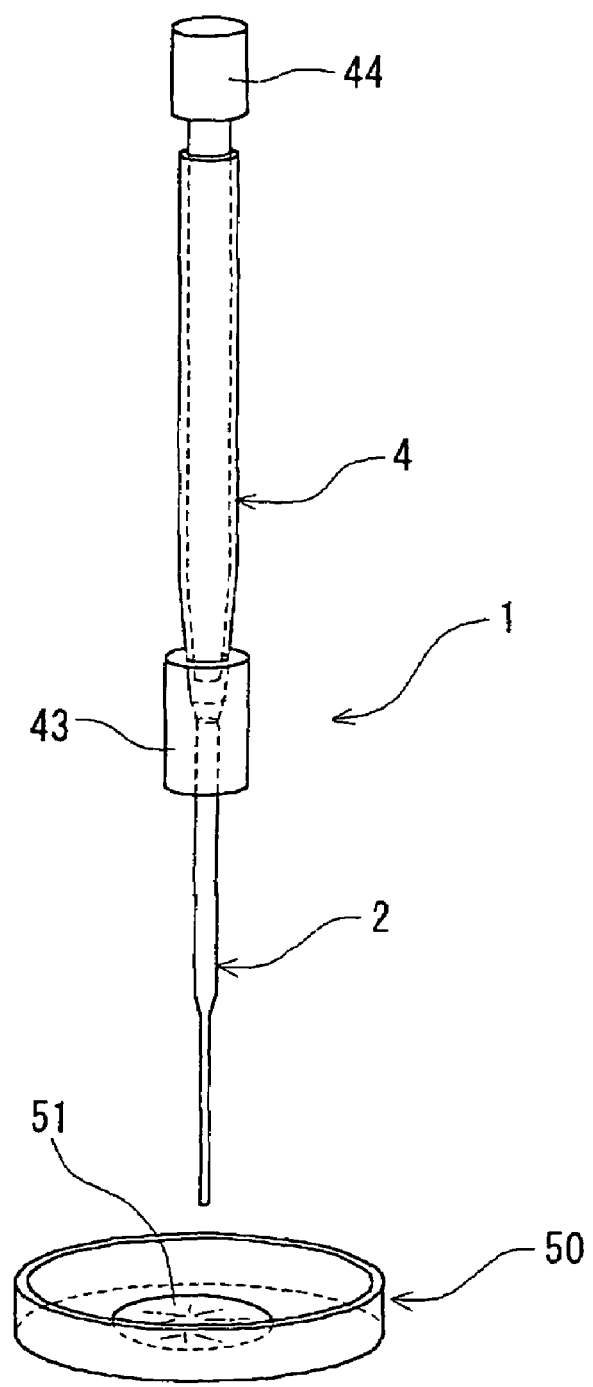
FIG. 6 is an explanatory view for explaining an operation of the egg freezing and storing instrument of the present invention.
Figure 7:
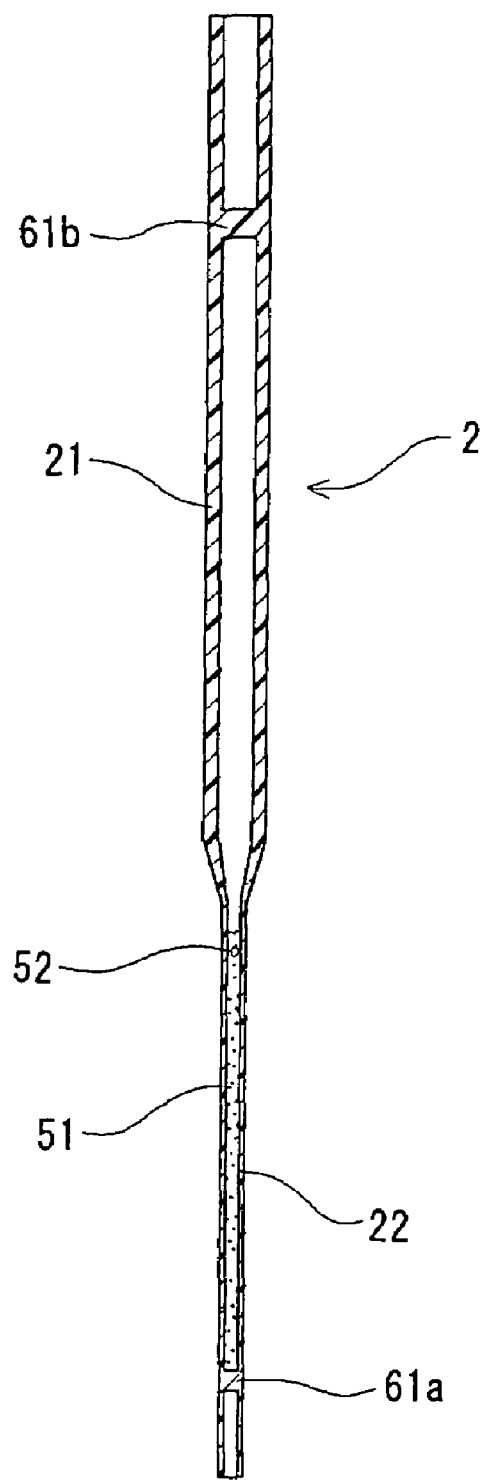
FIG. 7 is an explanatory view for explaining an operation of the egg freezing and storing instrument of the present invention.

Thereafter as shown in FIG. 6, the unit including the egg freezing and storing tube 2 and the sucking tool 4 mounted on the body part 21 of the egg freezing and storing tube 2 is prepared. Then the sucking tool 4 is operated under a microscope to collect an ovum 52 contained in the vitrified fluid disposed in a petri dish 50. The ovum 52 is collected into the small-diameter part 22 of the egg freezing and storing tube 2, together with the vitrified fluid. As shown in FIG. 7, it is preferable to collect the ovum 52, together with the vitrified fluid into the small-diameter part 22 by disposing the ovum 52 between the center of the small-diameter part 22 of the egg freezing and storing tube 2 and the rear end (base) of the small-diameter part 22. Then one side of the tube 2 is heat-sealed at a front portion of the small-diameter part 22 thereof to form a sealed portion 61*a*. Then the other side of the tube 2 is heat-sealed at a portion of the body part 21 to form a sealed portion 61*b*. Thereby the tube 2 is sealed at both ends thereof, as shown in FIG. 7.

Thereafter the tube 2 is removed from the sucking tool 4. Then as shown in FIG. 8, the front side of the small-diameter part 22 is inserted into the tubular part 31 of the metal protection member 3. Thereafter the protection member 3 is installed on the tube 2 with the body part 21 of the tube 2 held by the holding part 33 of the semi-tubular part 32. Finally the tube 2 is put in the liquid nitrogen tank to freeze and store the ovum 52.

An egg freezing and storing instrument according to another embodiment of the present invention will be described below.

Figure 9:
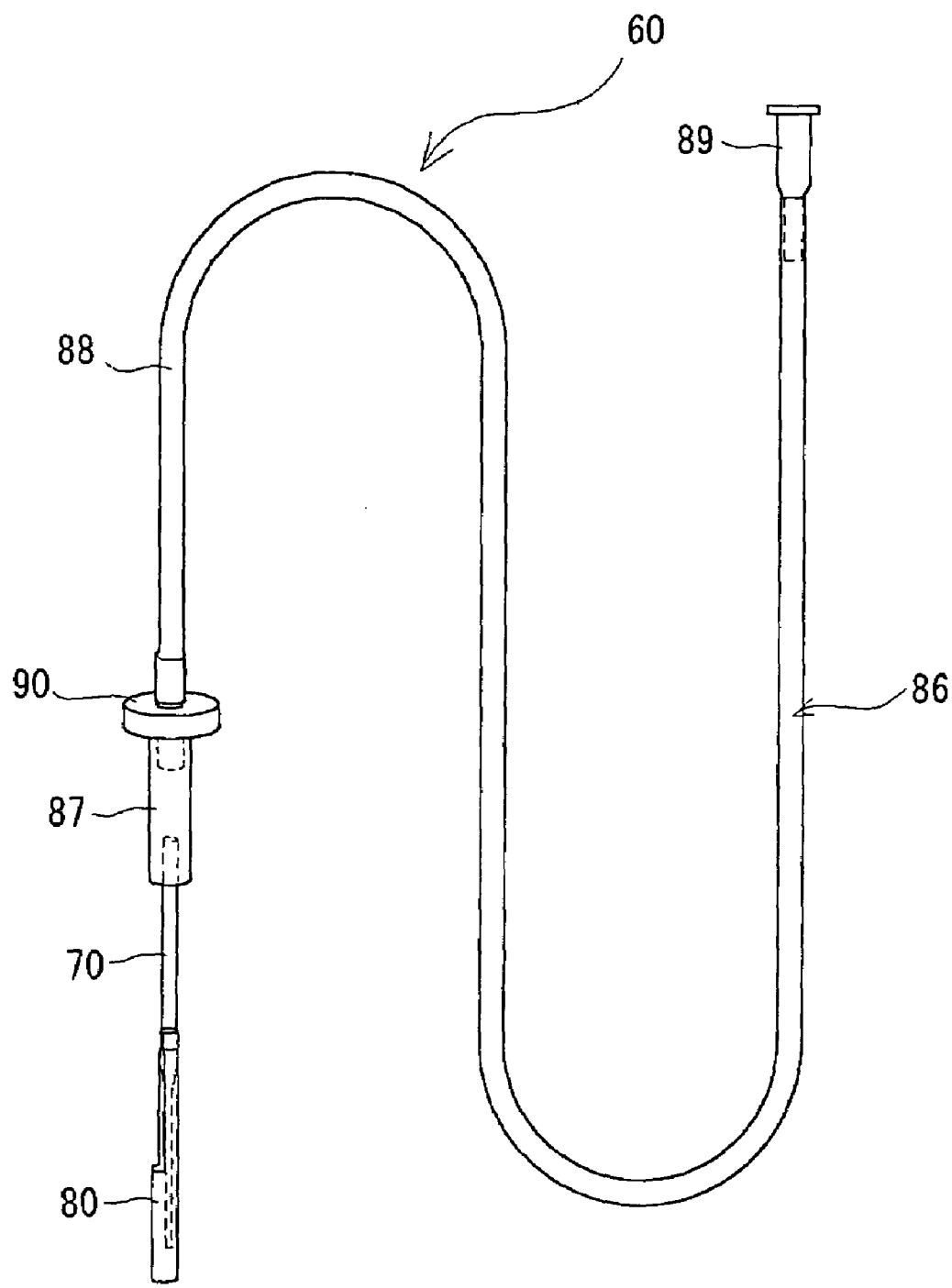
FIG. 9 is a perspective view showing another embodiment of an egg freezing and storing instrument of the present invention.
Figure 10:
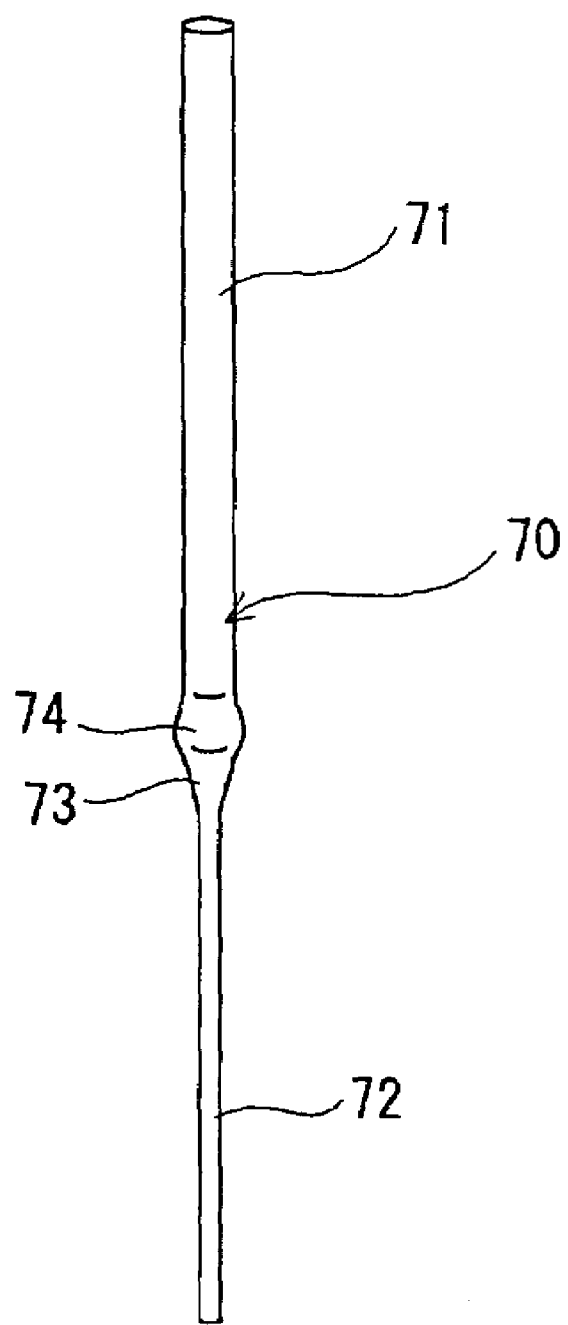
FIG. 10 is an enlarged side view showing an egg freezing and storing tube for use in the egg freezing and storing instrument shown in FIG. 9.
Figure 11:
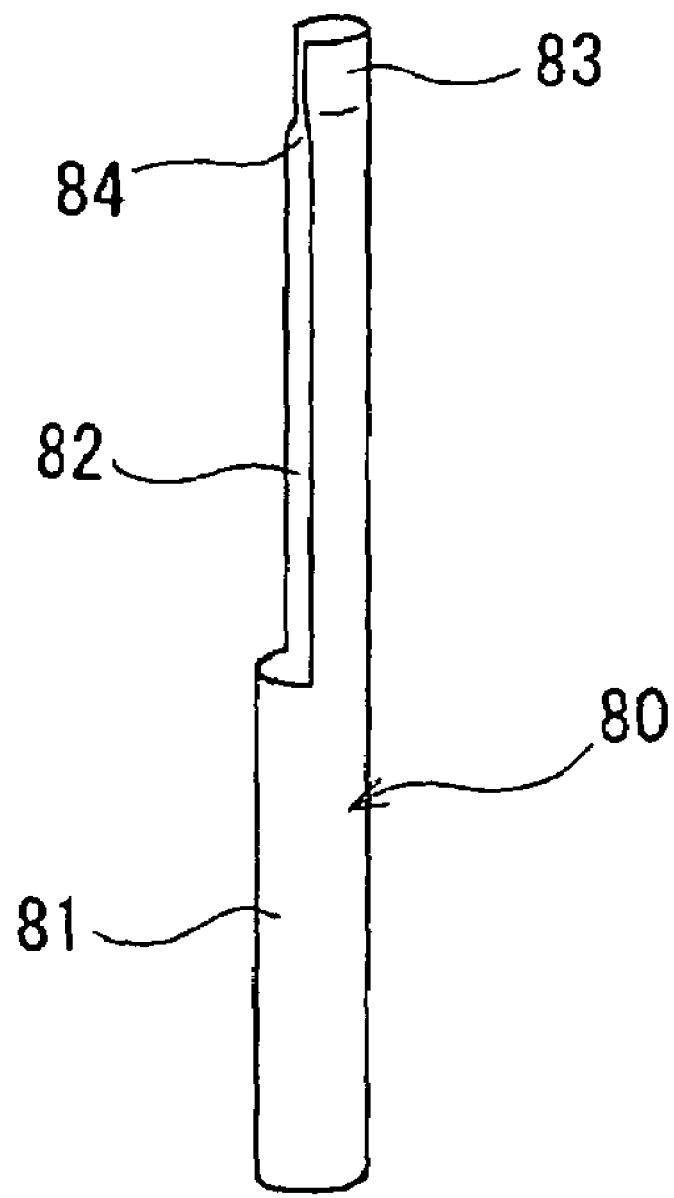
FIG. 11 is an enlarged view showing a cylindrical protection member for use in the egg freezing and storing instrument shown in FIG. 9.
Figure 12:
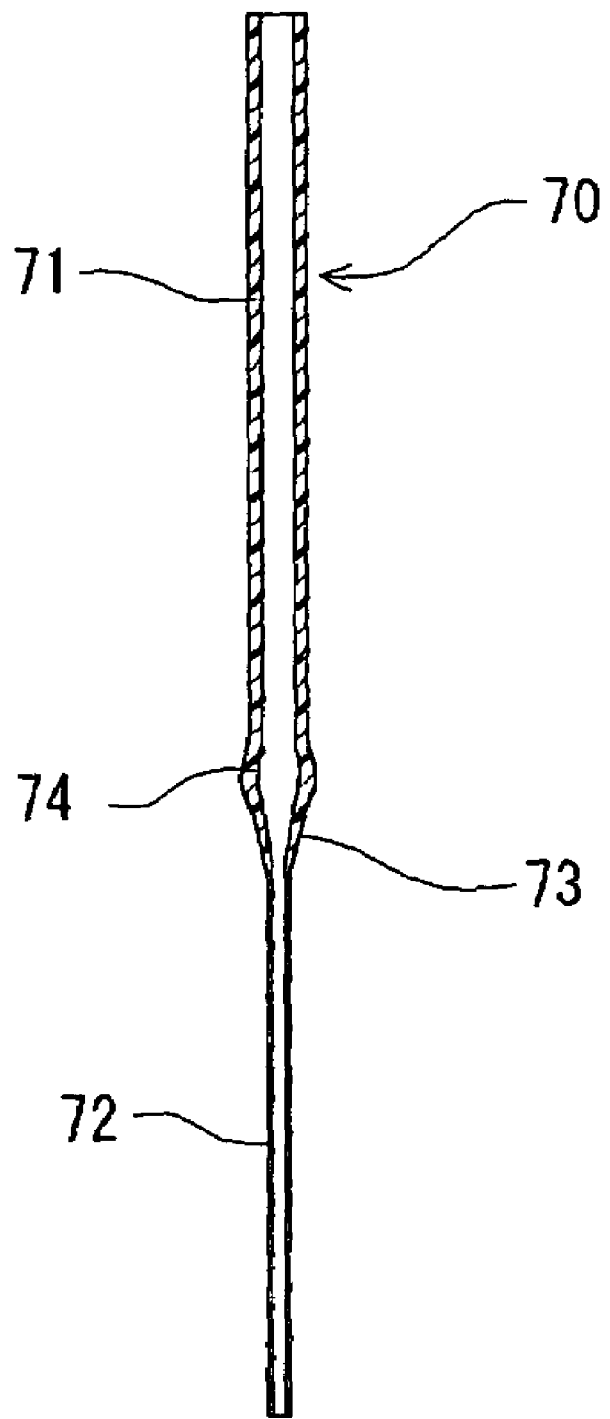
FIG. 12 is an enlarged sectional view showing the egg freezing and storing tube shown in FIG. 10.
Figure 13:
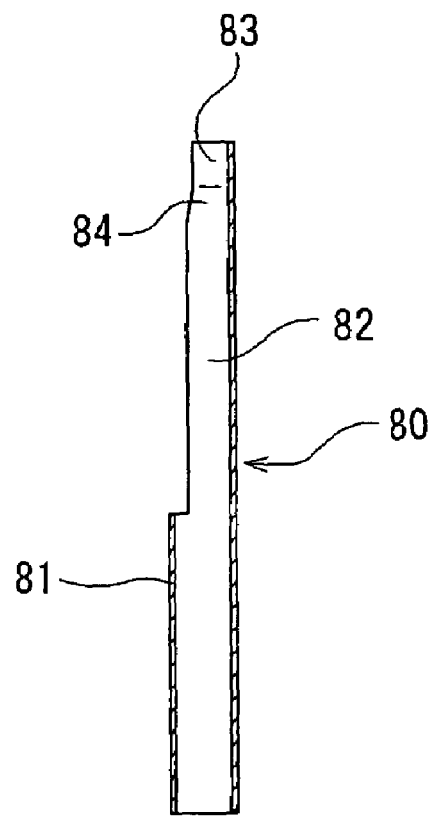
FIG. 13 is an enlarged sectional view showing the cylindrical protection member shown in FIG. 11.
Figure 14:
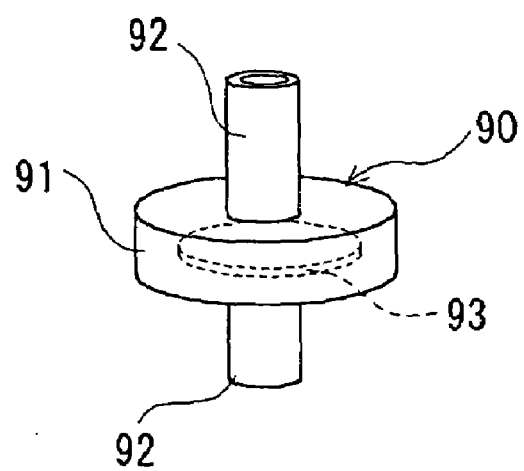
FIG. 14 is an enlarged view showing a filter part constituting an egg-collecting sucking tool for use in the egg freezing and storing instrument shown in FIG. 9.

FIG. 9 is a perspective view showing another embodiment of an egg freezing and storing instrument of the present invention. FIG. 10 is an enlarged side view showing an egg freezing and storing tube for use in the egg freezing and storing instrument shown in FIG. 9. FIG. 11 is an enlarged view showing a cylindrical protection member for use in the egg freezing and storing instrument shown in FIG. 9. FIG. 12 is an enlarged sectional view showing the egg freezing and storing tube shown in FIG. 10.

An egg freezing and storing instrument 60 of the present invention has an egg freezing and storing tube 70 which is made of a liquid nitrogen-resistant material and can be heat-sealed; and a metal cylindrical protection member 80, made of the liquid nitrogen-resistant material and mounted on the egg freezing and storing tube 70, for protecting the egg freezing and storing tube 70. The egg freezing and storing tube 70 has a body part 71 and an egg-storing small-diameter part 72 having a smaller outer diameter than the body part 71 and having an inner diameter of 0.1 mm to 0.5 mm. The egg freezing and storing tube 70 has a front-side heat-sealable portion at which the small-diameter part 72 can be heat-sealed at a front side of the small-diameter part 72 and a rear-side heat-sealable portion at which the body part 71 can be heat-sealed at a rear side of the body part 71, after an egg is collected in the egg-storing small-diameter part 72 thereof. The cylindrical protection member 80 has a tubular part 81 for accommodating the front side of the small-diameter part 72 of the egg freezing and storing tube 70; a semi-tubular part 82, disposed at a rear end of the tubular part 81, for accommodating a portion of the small-diameter part 72 of the egg freezing and storing tube 70 not accommodated in the tubular part 81 and a front portion of the body part 71; and a holding part 83, disposed at a rear end of the semi-tubular part 82, for holding the body part 71 of the egg freezing and storing tube 70. The cylindrical protection member 80 is slidable to the rear side of the tube 70 to allow the small-diameter part 72 to be exposed to the outside from a front end of the cylindrical protection member 80. A slip-off prevention part 74 for preventing the cylindrical protection member 80 from slipping off from the egg freezing and storing tube 70 is formed on the body part 71 of the egg freezing and storing tube 70 or in the vicinity of a boundary between the body part 71 and the small-diameter part 72.

It is preferable that the egg freezing and storing instrument 60 has an egg-collecting sucking tool 86 including a connection part 87 that can be connected to the rear end of the body part 71 of the egg freezing and storing tube 70; a tube 88 mounted on the connection part 87 directly or indirectly; and a mouthpiece 89 mounted on the tube 88. The above-described egg-collecting sucking tool 4 of a syringe type can be used as the egg-collecting sucking tool 86.

As shown in FIG. 9, the egg freezing and storing instrument 60 of this embodiment has the egg freezing and storing tube 70, the cylindrical protection member 80 mounted on the egg freezing and storing tube 70, and the egg-collecting sucking tool 86.

The egg freezing and storing tube 70 of this embodiment is the same as the egg freezing and storing tube 2 in the fundamental construction thereof except that the body part 71 of the tube 70 has the slipoff prevention part 74. The egg freezing and storing instrument 60 is described below mainly about constructions thereof different from those of the egg freezing and storing tube 2.

As shown in FIG. 9, the egg freezing and storing tube 70 has the body part 71; the egg-storing small-diameter part 72 having a smaller diameter than the body part 71; a tapered part 73, interposed between the body part 71 and the egg-storing small-diameter part 72, tapering off toward the front end of the small-diameter part 72; and the slip-off prevention part 74 disposed in the vicinity of the boundary between the tapered part 73 and the front end of the body part 71.

When the above-described egg-collecting sucking tool of the syringe type is used for the egg freezing and storing tube 70, the full length of the egg freezing and storing tube 70 is set to favorably 50 to 100 mm. The length of the body part 71 is set to favorably 30 to 60 mm. The inner diameter of the body part 71 is set to favorably 1.0 to 3.0 mm and more favorably 1.6 to 1.8 mm. The thickness of the body part 71 is set to favorably 50 to 400 µm and more favorably 100 to 300 µm. The length of the small-diameter part 72 is set to favorably 20 to 50 mm and more favorably 30 to 40 mm.

When the egg-collecting sucking tool of the mouthpiece type is used for the egg freezing and storing tube 70, the full length of the egg freezing and storing tube 70 is set to favorably 110 to 150 mm. The length of the body part 71 is set to favorably 80 to 115 mm. The inner diameter of the body part 71 is set to favorably 1.0 to 3.0 mm and more favorably 1.6 to 1.8 ml. The thickness of the body part 71 is set to favorably 50 to 400 µm and more favorably 100 to 300 µm. The length of the small-diameter part 72 is set to favorably 20 to 50 mm and more favorably 30 to 40 mm. If the egg-collecting sucking tool is of the mouthpiece type as shown in FIG. 9, the egg freezing and storing instrument is used in a state similar to a pen-holding state. Thus it is preferable that the full length of the tube 70 is longer than that of the tube 2 for which the egg-collecting sucking tool of the syringe type is used.

As shown in FIGS. 9, 10, and 12, the body part 71 has substantially the same outer diameter over the full length thereof except the slip-off prevention part 74. The small-diameter part 72 has also the substantially same outer diameter over the full length thereof. Each of the body part 71 and the small-diameter part 72 may be gently tapered to the front end thereof. In the embodiment, the slip-off prevention part 74 is formed in the vicinity of the boundary between tapered part 73 and the front end of the body part 71. Instead, the slip-off prevention part 74 may be formed at a portion of the body part 71 rearward from the boundary between tapered part 73 and the front end of the body part 71.

The inner diameter of the body part 71 is set to favorably 1.5 to 2.0 mm and more favorably 1.6 to 1.8 mm. The thickness of the body part 71 is set to favorably 10 to 300 µm and more favorably 25 to 200 µm. The inner diameter of the small-diameter part 72 is set to 0.15 to 0.30 mm and favorably 0.20 to 0.285 mm. The thickness of the small-diameter part 72 is set to favorably 10 to 300 µm and more favorably 25 to 200 µm. It is favorable that the thickness of the small-diameter part 72 is set smaller than that of the body part 71.

An outer diameter and thickness transition region is formed in the tapered part 73. More specifically, in the tapered part 73, the outer diameter, inner diameter, and thickness of the tube 70 become gradually smaller toward the small-diameter part 72. The tapered part 73 serves as a means for preventing the tube 70 from kinking at the boundary between the body part and the small-diameter part.

The above-described materials are preferably used for forming the egg freezing and storing tube. The egg freezing and storing tube may consist of a plurality of layers, similarly to the tube 2.

The slip-off prevention part 74 of this embodiment is formed as a diameter-widened part 74 disposed at the front end of the body part 71 of the egg freezing and storing tube 70 and in the tapered part 73 thereof. The diameter-widened part 74 is so formed that the diameter thereof becomes gradually larger from the front end of the body part 71 to the tapered part 73. The outer diameter of the diameter-widened part 74 is set larger than the inner diameter of the holding part 83 which will be described later. This construction prevents the protection member 80 from moving toward the front end of the egg freezing and storing tube 70 after the slip-off prevention part 74 contacts the holding part 83. It is preferable that the outer diameter of the diameter-widened part 74 is set smaller than the inner diameter of the cylindrical protection member 80. In this embodiment, the diameter-widened part is formed integrally with the egg freezing and storing tube. But the slip-off prevention part does not necessarily have to be formed integrally with the egg freezing and storing tube, but may be formed by mounting a separate member on the egg freezing and storing tube. For example, an annular member may be attached to the egg freezing and storing tube to form the slip-off prevention part. The slip-off prevention part may have any configurations, provided that it prevents the holding part 83 from moving toward the front end of the egg freezing and storing tube 70.

It is preferable to graduate the egg freezing and storing tube to check the position of an ovum sucked thereto. It is preferable to graduate the egg freezing and storing tube to be installed on the egg-collecting sucking tool of the syringe type at positions of 5 mm, 8 mm, 24 mm, and 70 mm from the front end thereof. It is preferable to graduate the egg freezing and storing tube to be installed on the egg-collecting sucking tool of the mouthpiece type at positions of 5 mm, 8 mm, 24 mm, and 100 mm from the front end thereof. The above-described egg-storing tube 2 maybe graduated.

Similarly to the tube 2, the egg freezing and storing tube 2 has the front-side heat-sealable portion at which the small-diameter part 22 can be heat-sealed at the front side thereof and the rear-side heat-sealable portion at which the body part 21 can be heat-sealed at the rear side thereof, after an egg is collected in the egg-storing small-diameter part 22. In this embodiment, the tube 70 can be heat-sealed at every portion thereof. However, the heat-sealable portion is not limited to this construction. For example, as the heat-sealable portion (easy-to-seal portion), a thin portion which is to be heat-sealed may be formed at the front side of the small-diameter part 22 and at the rear side of the body part 21. As another example of the heat-sealable portion, an inner layer made of a heat-sealable material may be formed at the front side of the small-diameter part 22 and at the rear side of the body part 21.

The cylindrical protection member 80 will be described below.

The basic construction of the cylindrical protection member 80 is almost the same as the above-described cylindrical protection member 3 except that the configuration of the holding part 83 of the cylindrical protection member 80 is different from that of the holding part 33 of the cylindrical protection member 3. The cylindrical protection member 80 is described below mainly about constructions thereof different from those of the cylindrical protection member 3.

The metal cylindrical protection member 80 is mounted on the egg freezing and storing tube 70. The cylindrical protection member 80 has the tubular part 81 disposed at the front side thereof, the semi-tubular part 82 disposed at the rear side thereof, and the holding part 83 disposed at the rear side of the semi-tubular part 82. The tubular part 81 accommodates the front side of the small-diameter part 72 of the egg freezing and storing tube 70. The semi-tubular part 82 accommodates the portion of the small-diameter part 72 of the egg freezing and storing tube 70 not accommodated in the tubular part 81 and the front portion of the body part 71. It is preferable that the tubular part 81 and the semi-tubular part 82 have a construction similar to the above-described one respectively.

Figure 15:
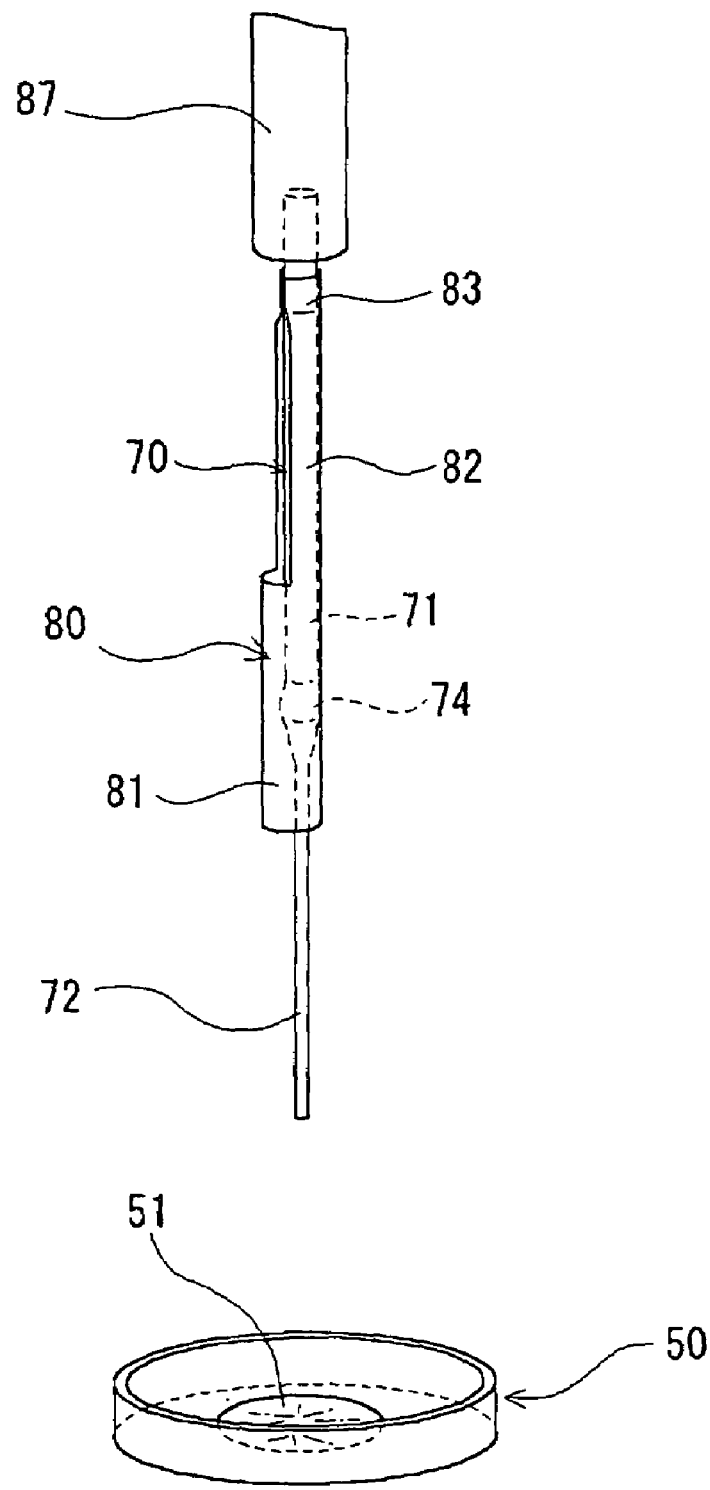
FIG. 15 is an explanatory view for explaining an operation of the egg freezing and storing instrument of the present invention.
Figure 16:
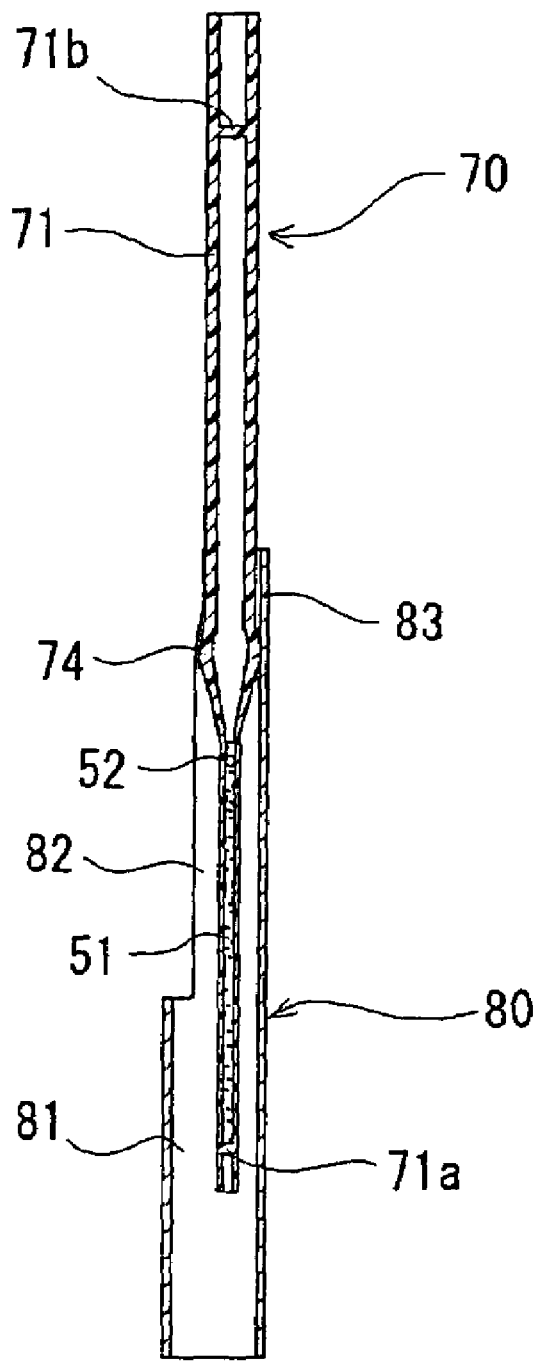
FIG. 16 is an explanatory view for explaining an operation of the egg freezing and storing instrument of the present invention.

The holding part 83 is formed by caulking the rear end of the semi-tubular part 82 along the outer surface of the body part 71 of the egg freezing and storing tube 70. The holding part 83 is mounted on the body part 71 of the tube 70 with the holding part 83 in dose contact with the body part 71 to hold the outer surface of the body part 71 of the tube 70. As shown in FIG. 15, the cylindrical protection member 80 is mounted on the body part 71 of the tube 70 in such a way that the cylindrical protection member 80 is slidable to allow the small-diameter part 72 to be exposed from the front end of the cylindrical protection member 80. More specifically, the holding part 83 dosely contacts and holds the body part 71 of the egg freezing and storing tube 70 to such an extent that the cylindrical protection member 80 is slidable on the body part 71 of the egg freezing and storing tube 70. The holding part 83 may have a construction similar to that of the above-described holding part 33. In this embodiment, a diameter-reduced part 84 whose diameter decreases gradually toward the rear end of the cylindrical protection member 80 is formed between the semi-tubular part 82 and the holding part 83. Therefore as shown in FIG. 16, the diameter-widened part 74 and the diameter-reduced part 84 engage each other with the tubular part 81 of the cylindrical protection member 80 accommodating the small-diameter part 72 of the tube 70 therein. Consequently the protection member 80 has difficulty in moving to the rear side of the tube 70.

The cylindrical protection member 80 serves as a means for protecting the tube 70 which has collected the egg, together with a vitrified fluid without inhibiting cooling of the egg. Therefore when the cylindrical protection member 80 is mounted on the tube 70, the collected egg-disposed range of small-diameter part 72 between the central position thereof and the rear end thereof is located within the length of the semi-tubular part 82. That is, the cylindrical protection member 80 is mounted on the tube 70 in such a way that the small-diameter part 72 accommodating the egg is exposed to the outside and easily capable of contacting liquid nitrogen.

The cylindrical protection member 80 is mounted on the tube 70 with the front end thereof unprojecting from the front end of the tubular part 81. Thus when the tube 70 on which the protection member 80 has been mounted is introduced into a liquid nitrogen-filled container from the small-diameter part 72, the front end of the small-diameter part 72 of the tube 70 does not contact the bottom surface of the liquid nitrogen-filled container. Therefore it is possible to prevent the tube 70 from kinking at the small-diameter part 72 or the tapered part 73 and thus prevent the tube 70 from being damaged.

The full length of the protection member 80 is set to favorably 20 to 70 mm, more favorably 30 to 50 mm, and most favorably 45 to 55 mm. The length of the tubular part 81 is set to favorably 5 to 40 mm, more favorably 5 to 20 mm, and most favorably 7 to 15 mm. The inner diameter of the tubular part 81 is set to favorably 2.0 to 4.0 mm and more favorably 2.5 to 3.5 mm. It is favorable that the tubular part 81 is circular, as shown in the drawings. But the tubular part 81 may be elliptically cylindrical or polygonally cylindrical. The thickness of the tubular part 81 is set to favorably 0.3 to 1.0 mm.

The length of the semi-tubular part 82 is set to favorably 10 to 40 mm and more favorably 25 to 35 mm. It is favorable that the inner circumference of the semi-tubular part 82 is ⅓ to ⅔ as small as that of the tubular part 81. It is favorable that the body part 71 of the tube 70 can be accommodated in the semi-tubular part 82 from the side face of the semi-tubular part 82. That is, the tube 70 can be mounted on the protection member 80 not from the opening at the rear end of the semi-tubular part 82 but from the axially long opening at the side face thereof. It is preferable that the semi-tubular part 82 is semicylindrical, as shown in the drawings. But the semi-tubular part 82 may be semi-elliptically cylindrical or semi-polygonally cylindrical. It is preferable that the material for the cylindrical protection member 80 is the same as that for the protection member 3. It is preferable that the length of the holding part 83 is 1.5 to 3.5 mm. It is preferable that the inner diameter of the holding part 83 is 1.5 to 2.0 mm.

The egg freezing and storing instrument 60 has the connection part 87 that can be connected to the rear end of the body part 71 of the egg freezing and storing tube 70; a tube 88 mounted on the connection part 87 directly or indirectly; and an egg-collecting sucking tool 86 having a mouthpiece 89 mounted on the tube 88. In using the sucking tool 86 of the mouthpiece type, an operator sucks the mouthpiece 89 to draw the ovum into the egg freezing and storing tube 70.

It is preferable that a filter part 90 is formed between the connection part 87 and the tube 88.

As shown in FIG. 9, the sucking tool 86 of this embodiment has the cylindrical connection part 87, the filter part 90 disposed between the connection part 87 and the tube 88, the tube 88, and the mouthpiece 89.

The connection part 87 is a cylindrical member. The connection part 87 is so configured that the body part 71 of the egg freezing and storing tube 70 is mounted on the connection part 87 at its one end. A port 92 of the filter part 90 can be mounted on the connection part 87 at its other end.

The filter part 90 has a body portion 91 in which a disk-shaped filter 93 is disposed and the port 92 formed on the front and rear surface of the body portion 91. It is preferable that the filter 93 is air-permeable and fluid-unpermeable. The connection part 87 can be mounted on one port 92. The tube 88 can be mounted on the other port 92.

It is preferable that the tube 88 is made of a flexible material such as silicone, polyvinyl chloride, and the like. It is preferable that the length of the tube 88 is set to such an extent that the egg freezing and storing instrument can be used in a state similar to a pen-holding state with the mouthpiece 89 in an operator's mouth.

The method of the present invention for freezing and storing an egg will be described below. The method for freezing and storing an egg is carried out in using the above-described egg freezing and storing instrument 85. FIG. 15 is an explanatory view for explaining an operation of the egg freezing and storing instrument of the present invention. FIG. 16 is an explanatory view for explaining an operation of the egg freezing and storing instrument of the present invention.

The storing method includes the steps of preparing an egg whose intracellular fluid has been replaced with an equilibrium fluid and whose extracellular fluid has been replaced with a vitrified fluid; exposing the small-diameter part 72 of the egg freezing and storing tube 70 to the outside by sliding the cylindrical protection member 80 to the rear side of the egg freezing and storing tube 70; collecting the egg into the small-diameter part 72 of the egg freezing and storing tube 70, together with the vitrified fluid; heat-sealing one side of the egg freezing and storing tube 70 at a front portion of the small-diameter part 72 which has collected the egg and heat-sealing the other side of the egg freezing and storing tube 70 at a portion of the body part 71; accommodating the small-diameter part 72 of the egg freezing and storing tube 70 in the cylindrical protection member 80 by sliding the cylindrical protection member 80 to the front side of the egg freezing and storing tube 70, after one side of the egg freezing and storing tube 70 is sealed or both the one side of the egg freezing and storing tube 70 and a portion of the body part 71 are sealed; and supplying the egg freezing and storing instrument 60 into a liquid nitrogen tank.

More specifically, the storing method includes the steps of preparing an egg whose intracellular fluid has been replaced with an equilibrium fluid and whose extracellular fluid has been replaced with a vitrified fluid; preparing a unit including the egg freezing and storing tube 70 constituting the egg freezing and storing instrument 60 and the sucking tool 86 mounted on the body part 71 of the egg freezing and storing tube 70; exposing the small-diameter part 72 of the egg freezing and storing tube 70 to the outside by sliding the cylindrical protection member 80 of the egg freezing and storing instrument 60 to the rear side of the egg freezing and storing tube 70; collecting the egg into the small-diameter part 72 of the egg freezing and storing tube 70, together with the vitrified fluid by operating the sucking tool 86; heat-sealing one side of the egg freezing and storing tube 70 at a front portion of the small-diameter part 72 and heat-sealing the other side of the egg freezing and storing tube 70 at a portion of the body part 71 with the sucking tool 86 mounted on the egg freezing and storing tube 70; accommodating the small-diameter part 72 of the egg freezing and storing tube 70 in the cylindrical protection member 80 by sliding the cylindrical protection member 80 to the front side of the egg freezing and storing tube 70, after the one side of the egg freezing and storing tube 70 is sealed or both the one side of the egg freezing and storing tube 70 and a portion of the body part 71 are sealed; removing the sucking tool 86 from the egg freezing and storing tube 70; and supplying the egg freezing and storing instrument 60 from which the sucking tool 86 has been removed into a liquid nitrogen tank.

The step of sealing the egg freezing and storing tube is performed with the sucking tool mounted on the egg freezing and storing tube. Thus it is possible to prevent bacteria from penetrating into the tube in which the egg has been collected.

The method of freezing and storing an egg will be described below by exemplifying the case in which an ovum is frozen to store them. Initially the ovum is collected at the tip of a pipette, and a work of replacing the intracellular fluid of the ovum with the equilibrium fluid is performed. Then a work of replacing the extracellular fluid with the vitrified fluid is performed.

Thereafter as shown in FIG. 9, a unit including the egg freezing and storing tube 70 constituting the egg freezing and storing instrument 60 and the sucking tool 86 mounted on the body part 71 of the egg freezing and storing tube 70 is prepared. Then as shown in FIG. 15, the cylindrical protection member 80 is slid toward the rear end of the egg freezing and storing tube 70 to expose the small-diameter part 72 to the outside. Then as shown in FIG. 15, the sucking tool 86 is operated under a microscope to collect an ovum 52 contained in a vitrified fluid 51 disposed in a petri dish 50. The ovum 52 is collected into the small-diameter part 72 of the egg freezing and storing tube 70, together with the vitrified fluid 51. It is preferable to collect the ovum 52, together with the vitrified fluid into the small-diameter part 72 by disposing the ovum 52 between the center of the small-diameter part 22 of the egg freezing and storing tube 70 and the rear end (base) of the small-diameter part 72. Then one side of the tube 70 is heat-sealed at a front portion of the small-diameter part 72 thereof to form a sealed portion 71a. Then the other side of the tube 2 is heat-sealed at a portion of the body part 21 to form a sealed portion 71b. Thereby the tube 70 is sealed at front and rear end thereof, as shown in FIG. 16. Thereafter as shown in FIG. 16, the cylindrical protection member 80 is slid toward the front end of the egg freezing and storing tube 70 to accommodate the small-diameter part 72 of the tube 70 inside the cylindrical protection member 80. Thereafter the egg freezing and storing instrument (the egg freezing and storing tube 70 and the cylindrical protection member 80) 60 is removed from the sucking tool 86 and put into the liquid nitrogen tank to freeze and store the ovum 52 therein.

The egg freezing and storing instrument of the present invention includes the egg freezing and storing tube which is made of the liquid nitrogen-resistant material and can be heat-sealed; and the metal cylindrical protection member, made of the liquid nitrogen-resistant material, for protecting the egg freezing and storing tube. The egg freezing and storing tube includes the body part; the egg-storing small-diameter part having a smaller outer diameter than the body part and having the inner diameter of 0.1 mm to 0.5 mm; the front-side heat-sealable portion at which the small-diameter part can be heat-sealed at the front side of the small-diameter part after the egg is collected in the egg-storing small-diameter part thereof; and the rear-side heat-sealable portion at which the body part can be heat-sealed at the rear side thereof, after the egg is collected in the egg-storing small-diameter part. The cylindrical protection member has the tubular part for accommodating the front side of the small-diameter part of the egg freezing and storing tube; and the semi-tubular part for accommodating the portion of the small-diameter part not accommodated in the tubular part and the front portion of the body part.

In this construction, after the egg is collected in the storing tube, both ends of the tube can be heat-sealed. Therefore it is possible to prevent permeation of bacteria into the tube while an operation of storing the egg in the tube and a vitrifying operation are being performed. Further even though the tube is brought into contact with liquid nitrogen, the egg does not contact the liquid nitrogen directly. In addition, since the egg can be collected in the small-diameter part of the tube, the egg can be cooled rapidly by the liquid nitrogen. Accordingly the egg can be securely placed in a vitrified state. Further the protection member prevents the tube from being damaged without inhibiting cooling of the tube, when the egg-collected tube is supplied to the liquid nitrogen tank.

The egg freezing and storing instrument according to another aspect of the present invention includes the egg freezing and storing tube which is made of the liquid nitrogen-resistant material and can be heat-sealed; and the metal cylindrical protection member, made of the liquid nitrogen-resistant material and mounted on the egg freezing and storing tube, for protecting the egg freezing and storing tube. The egg freezing and storing tube has the body part; the egg-storing small-diameter part having a smaller outer diameter than the body part and the inner diameter of 0.1 mm to 0.5 mm; the front-side heat-sealable portion at which the small-diameter part can be heat-sealed at the front side of the small-diameter part after the egg is collected in the egg-storing small-diameter part; and the rear-side heat-sealable portion at which the body part can be heat-sealed at the rear side thereof after the egg is collected in the egg-storing small-diameter part. The cylindrical protection member has the tubular part for accommodating the front side of the small-diameter part of the egg freezing and storing tube; the semi-tubular part, disposed at the rear end of the tubular part, for accommodating the portion of the small-diameter part not accommodated in the tubular part and the front portion of the body part; and the holding part, disposed at the rear end of the semi-tubular part, for holding the body part of the egg freezing and storing tube. The cylindrical protection member is slidable to the rear side of the egg freezing and storing tube to allow the small-diameter part to be exposed to the outside from the front end of the cylindrical protection member. The egg freezing and storing tube has the slip-off prevention part, for preventing the cylindrical protection member from slipping off from the front side of the egg freezing and storing tube, formed on the body part thereof or in the vicinity of the boundary between the body part thereof and the small-diameter part thereof.

In this construction, after the egg is collected in the storing tube, both ends of the tube can be heat-sealed. Therefore it is possible to prevent permeation of bacteria into the tube while an operation of storing the egg in the tube and a vitrifying operation are being performed. Further even though the tube is brought into contact with liquid nitrogen, the egg does not contact the liquid nitrogen directly. In addition, since the egg can be collected in the small-diameter part of the tube, the egg can be cooled rapidly by the liquid nitrogen. Accordingly the egg can be securely placed in a vitrified state. Further the protection member prevents the tube from being damaged without inhibiting cooling of the tube, when the egg-collected tube is supplied to the liquid nitrogen tank.

What is claimed is:

1. An egg freezing and storing instrument comprising:
   an egg freezing and storing tube which is made of a liquid nitrogen-resistant material and can be heat-sealed; and
   a metal cylindrical protection member for protecting said egg freezing and storing tube,
   wherein said egg freezing and storing tube comprises a body part; an egg-storing small-diameter part having a smaller outer diameter than said body part and having an inner diameter of 0.1 mm to 0.5 mm; a front-side heat-sealable portion at which said small-diameter part can be heat-sealed at a front side of said small-diameter part after an egg is collected in said egg-storing small-diameter part thereof; and a rear-side heat-sealable portion at which said body part can be heat-sealed at a rear side thereof, after said egg is collected in said egg-storing small-diameter part; and
   said cylindrical protection member has a tubular part for accommodating said front side of said small-diameter part of said egg freezing and storing tube; and a semi-tubular part for accommodating a portion of said small-diameter part of said egg freezing and storing tube not accommodated in said tubular part and a front portion of said body part.

2. An egg freezing and storing instrument according to claim 1, further comprising an egg-collecting sucking tool having a connection part to which a rear end of said body part of said egg freezing and storing tube can be connected.

3. An egg freezing and storing instrument according to claim 1, wherein said semi-tubular part of said cylindrical protection member has a holding part for holding said body part of said egg freezing and storing tube.

4. An egg freezing and storing instrument comprising:
   an egg freezing and storing tube which is made of a liquid nitrogen-resistant material and can be heat-sealed; and
   a metal cylindrical protection member mounted on said egg freezing and storing tube, for protecting said egg freezing and storing tube,
   wherein said egg freezing and storing tube comprises a body part; an egg-storing small-diameter part having a smaller outer diameter than said body part; a front-side heat-sealable portion at which said small-diameter part can be heat-sealed at a front side of said small-diameter part after an egg is collected in said egg-storing small-diameter part; and a rear-side heat-sealable portion at which said body part can be heat-sealed at a rear side thereof after said egg is collected in said egg-storing small-diameter part,
   said cylindrical protection member has a tubular part for accommodating said front side of said small-diameter part of said egg freezing and storing tube; a semi-tubular part, disposed at a rear end of the tubular part, for accommodating a portion of said small-diameter part of said egg freezing and storing tube not accommodated in said tubular part and a front portion of said body part; and a holding part, disposed at a rear end of said semi-tubular part, for holding said body part of said egg freezing and storing tube, said cylindrical protection member is slidable to a rear side of said egg freezing and storing tube to allow said small-diameter part to be exposed to the outside from a front end of said cylindrical protection member; and said egg freezing and storing tube has a slip-off prevention part, for preventing said cylindrical protection member from slipping off from said egg freezing and storing tube, formed on said body part thereof or in the vicinity of a boundary between said body part thereof and said small-diameter part thereof.

5. An egg freezing and storing instrument according to claim 4, wherein said slip-off prevention part is formed as a diameter-widened part formed in said body part of said egg freezing and storing tube or in the vicinity of a boundary between said body part and said small-diameter part.

6. An egg freezing and storing instrument according to claim 4, further comprising an egg-collecting sucking tool having a connection part to which a rear end of said body part of said egg freezing and storing tube can be connected.

7. An egg freezing and storing instrument according to claim 4, further comprising an egg-collecting sucking tool including a connection part that can be connected to a rear end of said body part of said egg freezing and storing tube; a tube mounted on said connection part directly or indirectly; and a mouthpiece mounted on said tube.

8. A method for freezing and storing an egg by using an instrument for freezing and storing an egg which comprises an egg freezing and storing tube which is made of a liquid nitrogen-resistant material and can be heat-sealed and has a body part, an egg-storing small-diameter part having a smaller outer diameter than said body part, and a metal cylindrical protection member mounted on said egg freezing and storing tube for protecting said egg freezing and storing tube and being slidable to a rear side of said egg freezing and storing tube to allow said small-diameter part to be exposed to the outside from a front end of said cylindrical protection member, and said egg freezing and storing tube has a slip-off prevention part for preventing said cylindrical protection member from slipping off from said egg freezing and storing tube, wherein said method comprising the steps of:

preparing said egg whose intracellular fluid has been replaced with an equilibrium fluid and extracellular fluid has been replaced with a vitrified fluid;

exposing said small-diameter part of said egg freezing and storing tube to the outside by sliding said cylindrical protection member to a rear side of said egg freezing and storing tube;

collecting said egg into said small-diameter part of said egg freezing and storing tube, together with said vitrified fluid;

heat-sealing one side of said egg freezing and storing tube at a front portion of said small-diameter part which has collected said egg and heat-sealing the other side of said egg freezing and storing tube at a portion of said body part;

accommodating said small-diameter part of said egg freezing and storing tube in said cylindrical protection member by sliding said cylindrical protection member to a front side of said egg freezing and storing tube after said one side of said egg freezing and storing tube is sealed or both said one side of said egg freezing and storing tube and a portion of said body part are sealed; and supplying said egg freezing and storing instrument into a liquid nitrogen tank.

9. A method for freezing and storing an egg by using an instrument for freezing and storing an egg which comprises an egg freezing and storing tube which is made of a liquid nitrogen-resistant material and can be heat-sealed and has a body part, an egg-storing small-diameter part having a smaller outer diameter than said body part, and a metal cylindrical protection member mounted on said egg freezing and storing tube for protecting said egg freezing and storing tube and being slidable to a rear side of said egg freezing and storing tube to allow said small-diameter part to be exposed to the outside from a front end of said cylindrical protection member, and an egg-collecting sucking tool having a connection part to which a rear end of said body part of said egg freezing and storing tube can be connected, and said egg freezing and storing tube has a slip-off prevention part for preventing said cylindrical protection member from slipping off from said egg freezing and storing tube, wherein said method comprising the steps of:

preparing said egg whose intracellular fluid has been replaced with an equilibrium fluid and extracellular fluid has been replaced with a vitrified fluid;

preparing a unit including said egg freezing and storing tube and said sucking tool mounted on a body part of said egg freezing and storing tube;

exposing a small-diameter part of said egg freezing and storing tube to the outside by sliding said cylindrical protection member to a rear side of said egg freezing and storing tube;

collecting said egg into said small-diameter part of said egg freezing and storing tube, together with said vitrified fluid by operating said sucking tool;

heat-sealing one side of said egg freezing and storing tube at a front portion of said small-diameter part and heat-sealing the other side of said egg freezing and storing tube at a portion of said body part with said sucking tool mounted on said egg freezing and storing tube;

accommodating said small-diameter part of said egg freezing and storing tube in said cylindrical protection member by sliding the cylindrical protection member to a front side of said egg freezing and storing tube after said one side of the egg freezing and storing tube is sealed or both said one side of said egg freezing and storing tube and a portion of said body part are sealed;

removing said sucking tool from said egg freezing and storing tube; and supplying said egg freezing and storing tube on which said protection member has been mounted into a liquid nitrogen tank.

* * * * *

UNITED STATES PATENT AND TRADEMARK OFFICE
CERTIFICATE OF CORRECTION

PATENT NO. : 7,316,896 B2  Page 1 of 1
APPLICATION NO. : 10/824605
DATED : January 8, 2008
INVENTOR(S) : Masashige Kuwayama et al.

It is certified that error appears in the above-identified patent and that said Letters Patent is hereby corrected as shown below:

Column 1, Line 45: change "endosably" to --enclosably--

Signed and Sealed this

Eighteenth Day of August, 2009

David J. Kappos
*Director of the United States Patent and Trademark Office*